United States Patent [19]  [11] 4,401,514
Kanzler et al.  [45] Aug. 30, 1983

[54] METHOD FOR THE RECOVERY OF FURFURAL, ACETIC ACID AND FORMIC ACID

[75] Inventors: Walter Kanzler; Johannes Schedler, both of Graz, Austria

[73] Assignee: Vereinigte Edelstahlwerke AG (VEW), Vienna, Austria

[21] Appl. No.: 245,076

[22] Filed: Mar. 18, 1981

[30] Foreign Application Priority Data

Apr. 10, 1980 [AT] Austria .................................. 1931/80

[51] Int. Cl.³ ...................... C07C 51/44; C07C 51/48; C07D 307/50
[52] U.S. Cl. .......................................... 203/15; 203/16; 203/17; 203/63; 203/77; 203/91; 203/DIG. 6; 159/47.3; 162/16; 422/197; 422/198; 422/202; 422/206; 549/489; 549/490; 562/513; 562/608; 562/609
[58] Field of Search .................. 159/47 WR; 562/513, 562/607–609; 162/14–16; 422/197, 198, 202, 203, 206; 203/43, 14–16, 91, 73, DIG. 6, 70, 63, 77; 549/483, 489, 490

[56] References Cited

U.S. PATENT DOCUMENTS

| | | | |
|---|---|---|---|
| 1,838,109 | 12/1931 | Richter | 162/16 |
| 1,870,665 | 8/1932 | Audibert | 422/197 |
| 2,076,184 | 4/1937 | Othmer | 203/16 |
| 2,107,527 | 2/1938 | Evans et al. | 203/16 |
| 2,886,573 | 4/1959 | Voltz | 422/198 |
| 3,040,094 | 6/1962 | Stine et al. | 562/513 |
| 3,607,125 | 9/1971 | Kydd | 422/197 |
| 3,764,462 | 10/1973 | Baierl | 162/16 |
| 3,904,484 | 9/1975 | King | 203/DIG. 6 |
| 4,143,066 | 3/1979 | Kalcevic | 562/513 |
| 4,143,702 | 3/1979 | Barr | 422/198 |

Primary Examiner—Wilbur L. Bascomb, Jr.
Attorney, Agent, or Firm—Werner W. Kleeman

[57] ABSTRACT

A method of recovering or extracting chemicals, such as furfural, formic acid, acetic acid and other organic compounds from acidic hydrolysates of plants or vegetable matter, especially spent sulfite liquors after conversion of the pentosans into pentoses and then into furfural by heating the hydrolysate in an acidic environment. The conversion of the pentosans pentoses into furfural, preferably with acidulation, is accomplished in a counterflow or countercurrent flow heat exchanger and a reactor, preferably a tubular reactor. The hydrolysate which has additionally been heated and converted in the reactor is used as a heating medium or heat carrier for heating up the hydrolysate which is converted in the counterflow heat exchanger, whereupon there is recovered as the distillate furfural in conjunction with the formic acid, acetic acid and the like.

14 Claims, 1 Drawing Figure

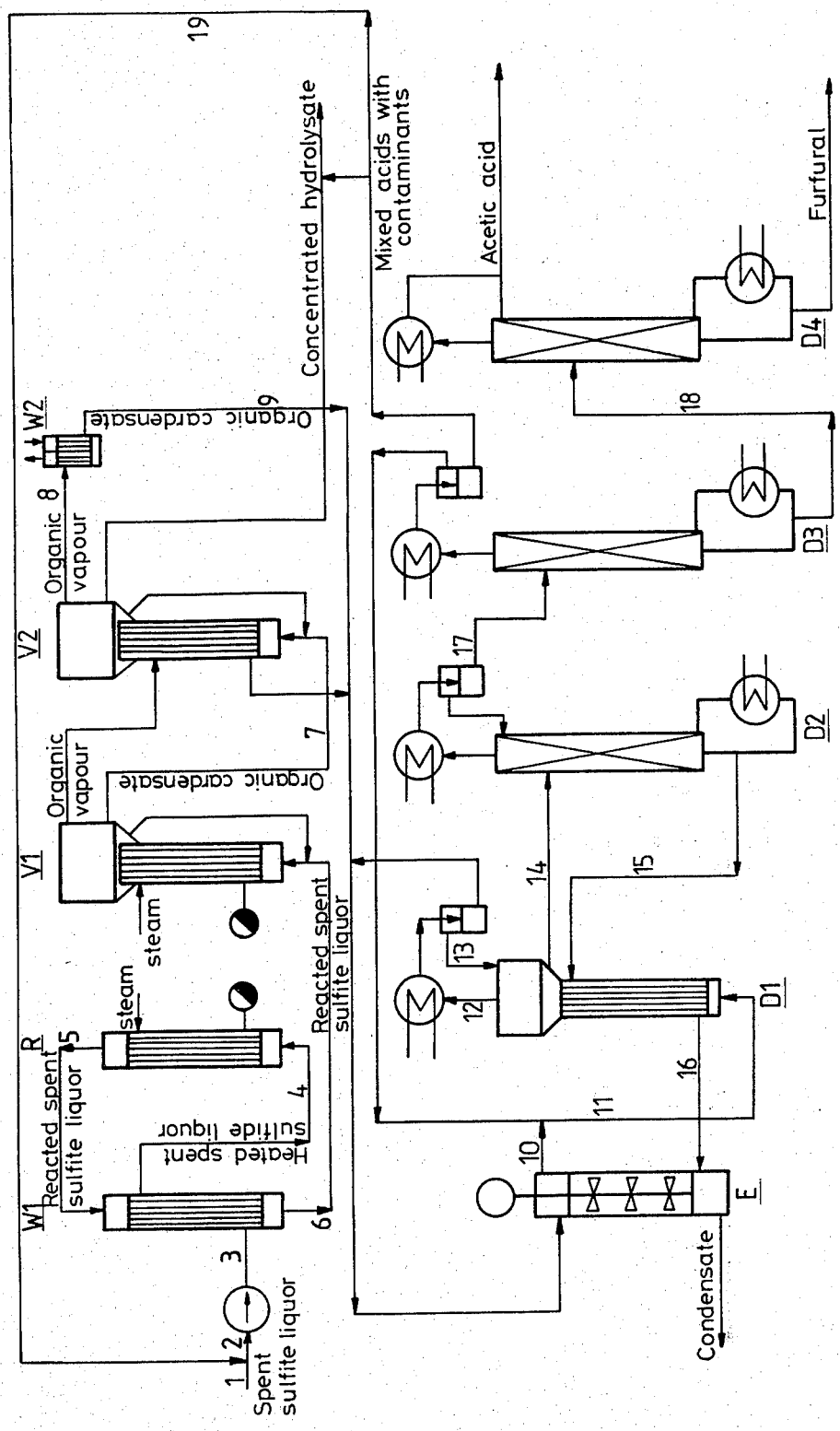

METHOD FOR THE RECOVERY OF FURFURAL, ACETIC ACID AND FORMIC ACID

CROSS REFERENCE TO RELATED APPLICATION

This application is related to our commonly assigned, copending U.S. application Ser. No. 239,200, filed Mar. 2, 1981, entitled "Method of Extracting Chemicals".

BACKGROUND OF THE INVENTION

The present invention relates to a new and improved method of extracting or recovering furfural, acetic acid and formic acid and other organic compounds from acidic hydrolysates of plants or vegetable matter.

Furfural can be obtained by the hydrolysis of pentosan-containing plants or their waste products. The plant or vegetable material is treated in the presence of acidic conditions at temperatures below 200° C. in a hydrolysis apparatus (cooker). Thereafter the furfural is obtained by treatment with steam (approximately 20 tons steam per ton furfural). These techniques are extremely energy consuming and, thus, usually in the furfural installations or plants, the plant material which has been cooked out is combusted following the hydrolysis and the heat of combustion is beneficially employed for generating the required steam.

In cellulose plants the recovery of cellulose is of primary importance and, generally, the pentosans together with the lignin and other hydrolysis products in the spent liquor are concentrated and combusted. In particular, during the hydrolysis or disintegration of deciduous wood and young plants, typically year old plants, there are combusted large quantities of pentosans (approximately 20% of the raw material). Therefore, numerous experiments have already been carried out for the purpose of extracting furfural from spent or waste sulfite liquors by converting the pentosans, and there has been performed a pressurised heating of the spent sulfite liquors at 150° C. to 180° C. for a number of hours with subsequent distillation of the spent sulfite liquor. Due to the long heating of the spent sulfite liquor a large quantity of the extracted or recovered furfural is again decomposed. Furthermore, the distillation of the furfural from the spent sulfite liquor requires large quantities of steam, and specifically, in order to extract 1 ton of furfural there are required 50 to 60 tons of steam.

In Austrian Pat. No. 356,509 there is disclosed a method wherein the substance contents of spent sulfite liquors and their vapour condensates can be economically recovered by extraction with liquid ion exchangers. The drawback of this prior art method resides in the fact that while there can be recovered completely the acetic acid which is formed during the hydrolysis or solubilisation, nonetheless the pentosans are still combusted in the form of xylose or wood sugar.

SUMMARY OF THE INVENTION

Therefore, with the foregoing in mind it is a primary object of the present invention to provide a new and improved method of extracting chemicals, especially furfural, formic acid, acetic acid and other organic compounds from acidic hydrolysates of plants, in a manner which does not suffer from the aforementioned drawbacks and limitations of the prior art proposals.

Another and more specific object of the present invention is directed to a new and improved method wherein a large part of the pentosans contained in the hydrolysates, for instance the spent or waste sulfite liquors, can be extracted in the form of furfural, and the pentosans can be converted as quickly as possible into furfural without encountering greater losses due to decomposition, and the recovered furfural can be extracted in an extremely energy saving manner.

Now in order to implement these and still further objects of the invention, which will become more readily apparent as the description proceeds, the method of the invention for the recovery of furfural, formic acid, acetic acid and other organic compounds from acidic hydrolysates of plants, especially spent waste sulfite liquors following conversion of the pentosans into furfural by heating the hydrolysate in an acidic environment, essentially resides in the conversion of the pentosans into furfural, preferably with acidification, is carried out in a counterflow heat exchanger and a reactor, preferably a tube or tubular reactor. The hydrolysate which is additionally heated and converted in the reactor is used as the heating medium for heating up the unconverted hydrolysate in the counterflow heat exchanger. Thereafter there can be recovered the furfural together with the formic acid, acetic acid and the like as the distillate.

The xylose or wood sugar contained in the hydrolysate is converted into furfural in the reactor. The hydrolysate effluxing from the reactor thereafter delivers its heat in a counterflow heat exchanger to the untreated hydrolysate, so that the latter is heated-up to several degrees below the conversion temperature. The residual quantity of heat is then supplied to the reactor through a jacket heater or an internally situated heating register. The treated hydrolysate is then delivered to a preferably multi-stage evaporation installation where the hydrolysate is concentrated to a concentration of about 50% and thereafter can be combusted. The vapours which are formed during the evaporation now almost completely contain the furfural present in the converted hydrolysate and the volatile acids.

If the conversion of xylose into furfural is accomplished in the reactor at temperatures between 220° C. and 300° C., and the speed for forming the furfural is sufficient, then the decomposition of furfural may be reduced when using the inventive method.

At a temperature beyond 200° C. there should be maintained a residence time which is less than 10 minutes, preferably less than 1 minute, of the hydrolysate in the reactor. As a result there can be obtained a particularly high yield.

An especially simple variant of the method can be realised, while at the same time enabling utilisation of the produced organic acids, i.e. a part of the formic acid and/or acetic acid obtained from the distillate is introduced upstream of the reactor to the hydrolysate.

The distillate which is recovered by the present invention e.g., containing acetic acid, formic acid and furfural, according to a further feature of the invention, is extracted by an extracting agent containing a 10 to 80% solution of phosphine oxide, preferably trioctyl phosphine oxide in a solvent, preferably an aliphatic hydrocarbon having a boiling point between 120° C. and 150° C. The charged or loaded extracting agent obtained according to this method step can be processed in a particularly simple manner, and the extracting agent mixture can be regenerated by distillation and the predominant part of the water which has dissolved in the charged extracting agent can be distilled off. Thereafter, if desired at a reduced or negative pressure, there can be distilled off a mixture, preferably an azeotrope composed of furfural, the acids, contaminants and the solvent. During the condensation of such mixture of the head products there are formed at least two phases. One of these phases consists of the diluting agent and the other of the products and contaminants, and there possibly can be separated out furfural in a separate phase.

Particularly at a low content of formic acid there is distilled off, according to the invention, from the product mixture containing the extracting agent during the distillation, a mixture, preferably an azeotrope composed of contaminants, water, formic acid and acetic acid as well as traces of furfural, and if desired this mixture can be delivered upstream of the reactor to the hydrolysate, and thereafter the mixture remaining in the bottom or sump and containing the acetic acid and furfural can be distillatively separated.

Also it has been found to be particularly advantageous if there is distilled off of the product mixture obtained during the installation of the extracting agent a mixture, preferably an azeotrope, containing contaminants, water, traces of formic acid, acetic acid and furfural. Thereafter there is added thereto an entraining agent, preferably di-n-propyl ether or ethyl-n-butyl ether for the water, and the water is then distilled off in conjunction with the entraining agent.

BRIEF DESCRIPTION OF THE DRAWING

The invention will be better understood and objects other than those set forth above, will become apparent when consideration is given to the following detailed description thereof. Such description makes reference to the annexed drawing wherein the single FIGURE of the drawing schematically shows a flow diagram of apparatus which can be used in practicing the inventive method.

DETAILED DESCRIPTION OF THE PREFERRED EMBODIMENTS

The invention now will be further explained based upon an example and the accompanying flow chart.

EXAMPLE

A spent sulfite liquor of a magnesium bisulfite cooking liquor of deciduous wood possessed a pH-value of 1.6 and contained, amon other things, 50 g/l xylose, 17 g/l acetic acid and 0.6 g/l formic acid. This spent sulfite liquor introduced at 1 was acidified (at 2) with an acidic mixture and introduced by conduit 3 into a counterflow heat exchanger W1 where it was brought to a pressure of about 80 bar by means of a pump and heated to 270° C. The flow rate amounted to 125 m³/h. The heated spent sulfite liquor was conveyed through 4 to the reactor R where it flowed at a velocity of 1 m/sec through the reactor R and thus was heated to 280° C. With a residence time of about 20 seconds there was formed 20 g/l furfural. This spent sulfite liquor effluxing from the reactor R again flowed to the counterflow heat exchanger W1 through conduit 5 and delivered its heat to the fresh spent sulfite liquor. After transport to the evaporation installation V1 and V2 through conduits 6 and 7, respectively, the spent sulfite liquor of about 10% by weight dry substance was evaporated or concentrated to approximately 50% by weight dry substance and underwent combustion. The vapours were carried to the heat exchanger W2 by pipe 8 where they were condensed and were delivered thereafter by conduit 9 to the extractor E where 100 m³/h vapour condensate having a content of about 20 g/l furfural, 17 g/l acetic acid and 0.6 g/l formic acid was brought into contact in one hour with 100 m³ of a 30% by weight solution of trioctyl phosphine oxide in undecane in countercurrent flow. After transport to distillation unit D1 by pipes 10 and 11 there was distilled off from the charged extracting agent, at 12, a mixture (an azeotrope) composed of undecane and water. After the condensation and phase separation the undecane was recycled back to the evaporator D1 through 13. The charged extraction agent, from which there now was removed the major proportion of water, passes through conduit 14 and is regenerated in the distillation column D2 and after passing through pipe 15 and transferring its heat in the evaporator D1 again was recycled back to the extractor E by means of conduit 16.

At the head of the column D2 there was condensed a mixture of undecane, furfural, acetic acid, formic acid, water and contaminants and the phases were separated in a separator, with the undecane being infed introduced as reflux to the column D2.

Thereafter the product mixture was transferred by means of pipe 17 and subjected to a further distillation in the column D3, and there was driven out a mixture (an azeotrope) composed of the water, the formic acid, a small amount of the acetic acid and the contaminants. The product mixture is now free of water and only consists of acetic acid and furfural which can be conveyed by conduit 18 to and separated by distillation in the column D4. From 125 m³ spent sulfite liquor there was recovered 2000 kg. furfural and 1800 kg. acetic acid. The acidic mixture and water driven out in the column D3, can be transferred by pipe 19 and used for the acidification of the spent sulfite liquor.

While there are shown and described present preferred embodiments of the invention, it is to be distinctly understood that the invention is not limited thereto, but may be otherwise variously embodied and practiced within the scope of the following claims. ACCORDINGLY,

What we claim is:

1. In a method of producing, recovering and separating furfural, acetic acid, formic acid and other organic compounds from acid treatment of plant material including the steps of acid hydrolysis of pentosans present in the plant material to form pentoses containing xylose, thereafter forming furfural from the pentose present in the plant hydrolysate and distillation of the furfural, the improvement comprising the steps of:
   (a) introducing to and heating an acidified aqueous solution of a plant material hydrolysate in a counterflow heat exchanger;
   (b) conveying the heated acidified hydrolysate solution from said counterflow heat exchanger to a reactor and converting xylose to furfural at a temperature range between about 220° C. and 300° C. at a residence time of less than 10 minutes to avoid decomposition of said furfural;
   (c) returning the reacted hydrolysate solution to the counterflow heat exchanger to supply heat to freshly introduced acidified hydrolysate solution; and
   (d) distilling the reacted hydrolysate solution to recover furfural, formic and acetic acids.

2. The method as defined in claim 1, further including the steps of:

using as the reactor a tubular reactor.

3. The method as defined in claim 1, wherein: the residence time of the hydrolysate
in the reactor is less than 1 minute and while exposed to a temperature exceeding about 200° C.

4. The method as defined in claim 1, further including the steps of:

preparing the acidified hydrolysate solution of step (a) by feeding to an hydrolysate a portion of at least any one of the formic acid and acetic acid obtained from the distillation of step (d).

5. The method as defined in claim 1, wherein:

the reaction product of step (b) comprises formic acid, acetic acid and furfural, extracting said formic acid, acetic acid and furfural with an extracting agent mixture containing a 10 to 80% by weight solution of a phosphine oxide in a solvent at a boiling point between 120° C. and 150° C.

6. The method as defined in claim 5, wherein:

the phosphine oxide is trioctyl phosphine oxide.

7. The method as defined in claim 5, wherein:

the solvent is an aliphatic hydrocarbon.

8. The method as defined in claim 5, further including the steps of:

regenerating the extracting agent mixture which includes water by distillation for the preparation of said extracting agent mixture; and distilling off a product mixture composed of furfural, formic acid, acetic acid, contaminants and the solvent.

9. The method as defined in claim 8, wherein:

the distillation of the product mixture is carried out at a negative pressure.

10. The method as defined in claim 8, wherein:

said product mixture is an azeotrope.

11. The method as defined in claim 8, further including the steps of:

adding to the product mixture an entraining agent for the water; and distilling off the water in conjunction with the entraining agent.

12. The method as defined in claim 11, wherein:

the entraining agent is selected from the group consisting essentially of di-n-propyl ether and ethyl-n-butyl ether.

13. The method as defined in claim 8, wherein said product mixture is further distilled to form a first acid mixture and a second acid mixture, said first acid mixture comprising an azeotrope of water, formic acid, acetic acid and traces of furfural and said second acid mixture comprising furfural and acetic acid.

14. The method as defined in claim 13, wherein said first acid mixture is used in preparing the acidified hydrolysate solution of step (a).

* * * * *